US00PP17508P3

(12) United States Plant Patent
Danziger

(10) Patent No.: US PP17,508 P3
(45) Date of Patent: Mar. 20, 2007

(54) **DOUBLE *IMPATIENS* PLANT NAMED 'DANMUBICRED'**

(50) Latin Name: *Impatiens walleriana*
Varietal Denomination: Danmubicred

(75) Inventor: Gabriel Danziger, Moshav Nir-Zvi (IL)

(73) Assignee: Danziger "Dan" Flower Farm, Post Beit Dagan (IL)

( * ) Notice: Subject to any disclaimer, the term of this patent is extended or adjusted under 35 U.S.C. 154(b) by 67 days.

(21) Appl. No.: 11/138,295

(22) Filed: May 27, 2005

(65) Prior Publication Data

US 2006/0272066 P1 Nov. 30, 2006

(51) Int. Cl.
*A01H 5/00* (2006.01)

(52) U.S. Cl. ..... Plt./317

(58) Field of Classification Search ..... Plt./317
See application file for complete search history.

*Primary Examiner*—Kent Bell
(74) *Attorney, Agent, or Firm*—Foley & Lardner LLP

(57) ABSTRACT

A new and distinct Double *Impatiens* plant named 'Danmubicred' characterized by having medium, upright and rounded growth habit; double, red and white bicolor flowers; yellow-green colored leaves and good branching.

2 Drawing Sheets

Botanical designation: *Impatiens walleriana.*
Variety denomination: 'Danmubicred'.

BACKGROUND OF THE INVENTION

The present invention relates to a new and distinct cultivar of Double *Impatiens* plant, botanically known as *Impatiens walleriana,* herein after referred to by the cultivar name 'Danmubicred'.

The new Double *Impatiens* cultivar is a product of a planned breeding program conducted by the Inventor, Gabriel Danziger, in Moshav Mishmar Hashiva, Israel. The objective of the breeding program is to develop a new Double *Impatiens* variety with medium, upright and rounded, growth habit, red and white bicolor flowers, yellow-green leaves, and good branching habit.

The new *Impatiens* cultivar 'Danmubicred' originated by selfing an *Impatiens walleriana* cultivar designated '348HF' (unpatented) in a controlled breeding program by the Inventor in 2002 in Moshav Mishmar Hashiva, Israel. 'Danmubicred' was discovered and selected by the Inventor in April of 2002 as a flowering plant within the progeny from the selfing of '348HF' in a controlled environment in Moshav Mishmar Hashiva, Israel.

Asexual reproduction of the new cultivar by stem tip cutting was first performed in July of 2002 in Moshav Mishmar Hashiva, Israel, and has demonstrated that the combination of characteristics as herein disclosed for the new cultivar are firmly fixed and retained through successive generations of asexual reproduction. The new cultivar reproduces true-to-type.

BRIEF DESCRIPTION OF THE INVENTION

The following traits have been repeatedly observed and are determined to be unique characteristics of the new Double *Impatiens* cultivar 'Danmubicred' which in combination distinguish this Double *Impatiens* as a new and distinct cultivar:

1. Medium, upright and rounded growth habit;
2. Double, red and white bicolor flowers;
3. Yellow-Green colored leaves; and
4. Good branching.

Plants of the new Double *Impatiens* 'Danmubicred' differ from plants of the parental cultivar, '348HF' (unpatented) in the following characteristics described in Table 1:

TABLE 1

| Trait | New Cultivar 'Danmubricred' | Parental Cultivar '348HF' |
|---|---|---|
| Flower color | Red group, RHS 52B<br>White group, RHS N155B | Red group, RHS 43B |
| Number of flowers | About 60 to 70 flowers in full bloom | About 60 to 70 flowers in full bloom |
| Leaf color (upper surface) | Yellow-Green group, RHS 146A | Green group, RHS 137A |
| Size of leaves | Length: 5 cm<br>Width: 3.5 cm | Length: 4.5 cm<br>Width: 3 cm |
| Growth and branching habit | Medium growth habit, Length: 18 cm<br>Strong branching | Medium growth habit, Length 20 cm<br>Strong branching |
| Flowering | Full blooming; 60 days after planting | Full blooming; 60 days after planting |

Of the many commercial cultivars known to the present Inventor, the most similar in comparison to the new Double *Impatiens* cultivar 'Danmubicred' is a Double *Impatiens* called 'Fiesta Sparkler Rose'. In side-by-side comparisons conducted in Moshav Mishmar Hashiva, Israel, plants of the 'Fiesta Sparkler Rose' differed from plants of 'Danmubicred' primarily in flower color and leaf size as provided in Table 2:

TABLE 2

| Trait | New Cultivar 'Danmubicred' | Comparison Cultivar 'Fiesta Sparkler Rose' |
|---|---|---|
| Flower color | Red group, RHS 52B<br>White group, RHS N155B | Red-purple group, RHS 61C |
| Length of leaves | 5 cm | 4 cm |
| Width of leaves | 3.5 cm | 3 cm |

BRIEF DESCRIPTION OF THE DRAWINGS

The accompanying colored photographs illustrate the overall appearance of the new Double *Impatiens* cultivar 'Danmubicred' showing the colors as true as is reasonably possible with colored reproductions of this type. Colors in the photographs may differ slightly from the color values cited in the detailed botanical description which accurately describe the color of the 'Danmubicred'.

The first photograph shows a side view perspective of a typical 'Danmubicred' potted plan at 3 months.

The second photograph shows a close-up view of typical flowers and leaves of 'Danmubicred' at 3 months.

DETAILED BOTANICAL DESCRIPTION

The Double *Impatiens* cultivar 'Danmubicred' has not been observed under all possible environmental conditions. The phenotype of the new cultivar may vary with variations in environment such as temperature, light intensity, and daylength, without any change in the genotype of the plant.

The aforementioned photographs, together with the following observations, measurements and values describe plants of the new Double *Impatiens* cultivar 'Danmubicred' as grown in a greenhouse in Moshav Mishmar Hashiva, Israel, under conditions which closely resemble those generally used in commercial practice. Plants of 'Danmubicred' are grown in a greenhouse with day temperatures ranging from 25° C. to 30° C. and night temperatures ranging from 18° C. to 25° C. Plants of 'Danmubicred' are fertilized up to a level of 100 ppm N, 35 ppm P and 120 ppm K. The age of the plants described is 8 weeks. The photographs and descriptions were taken during the winter when outdoor day temperatures ranged from 15° C. to 25° C. and outdoor night temperatures ranged from 10° C. to 15° C.

Color references are made with The Royal Horticultural Society Colour Chart (R.H.S.), 2001 edition, except where general colors of ordinary significance are used. Color values were taken under daylight conditions at approximately 12 noon in Moshav Mishmar Hashiva, Israel.

Classification:
- *Botanical.*—*Impatiens walleriana.*

Parentage:
- *Parental cultivar.*—Self-crossing of *Impatiens walleriana* cultivar designated '348HF' (unpatented).

Propagation:
- *Type.*—Stem tip cutting.
- *Time and temperature to initiate roots.*—Summer: 7 to 10 days at 25° C. Winter: 10 to 15 days at 21° C.
- *Time and temperature to produce a rooted cutting or liner.*—Summer: 15 to 18 days at 25° C. Winter: 18 to 21 days at 21° C.
- *Rooting habit and description.*—Fibrous roots, adventitious roots from cutting base.

Plant:
- *General appearance and form.*—Medium, upright and rounded.
- *Growth and branching habit.*—Very good branching.
- *Growth rate.*—2 months from rooted plant to a finished product in 12 to 13 cm pots.
- *Plant height.*—About 20 cm.
- *Plant width (spread).*—About 30 cm.

Lateral branches:
- *Quantity per plant.*—Primary Lateral shoots: About 7 Secondary lateral shoots: About 30.
- *Length.*—About 18 cm.
- *Diameter.*—About 0.8 cm.
- *Internode length.*—About 2 cm.
- *Strength.*—Strong, very stable.
- *Texture.*—Smooth.
- *Color.*—Upper surface: Yellow-green, RHS 144D. Lower surface: Yellow-green, RHS 144D.

Foliage:
- *Arrangement.*—Alternate.
- *Overall shape of leaf.*—Ovate.
- *Shape at apex.*—Acute.
- *Shape at base.*—Acute.
- *Length.*—About 5 cm.
- *Width.*—About 3 cm.
- *Margin.*—Toothed.
- *Texture.*—Upper surface: Smooth. Lower surface: Smooth.
- *Color of mature (developed) leaf.*—Upper surface: Yellow-Green, RHS 146A. Lower surface: Green, RHS 138B.
- *Color of immature (expanding) leaf.*—Upper surface: Yellow-Green, RHS 146A. Lower surface: Green, RHS 138B.

Venation:
- *Pattern.*—Midrib with secondary veins. Pinnate, only lower surface.
- *Color.*—Upper surface: Midrib: Yellow-Green, RHS 144B. Lower surface: Midrib: Green, RHS 138B Secondary veins: Green, RHS 138B.

Petiole:
- *Length.*—About 1 cm.
- *Diameter.*—About 3 mm.
- *Color.*—Upper surface: Green, RHS 142D. Lower surface: Green, RHS 142D.

Flower description:
- *Flower type and habit.*—Double flowers raised above the foliage.
- *Natural flowering season.*—Flowers at any day length. All year round in a greenhouse environment. Flowering is continuous from spring until fall in an outdoor garden.
- *Flowering response.*—8 weeks after planting of rooted cuttings.
- *Quantity of flowers.*—About 10 flowers and buds per stem.
- *Post production longevity.*—Up to six months.
- *Fragrance (if any).*—None.

Corolla:
- *Form.*—Double.
- *Shape.*—Rosette.
- *Length.*—About 3 cm.
- *Width.*—About 3 cm.
- *Depth.*—About 1.5 mm.
- *Color.*—Red-Purple, RHS 52B. Base: White, RHS N155B.

Buds:

*Rate of opening* (*from showing color to fully open flower*).—3 days.

*Length.*—About 1.2 cm.

*Diameter.*—At Apex: About 0.5 cm. At Base: About 1 cm.

*Shape.*—Rounded.

*Color.*—Red-purple, RHS N66A, with no changes between apex and base.

Petals:

*Quantity and arrangement per flower.*—About 32 petals, Arrangement: Imbricate.

*Lateral and base petal length.*—About 2 cm.

*Lateral and base petal width.*—About 2 cm.

*Overall shape.*—Obcordate.

*Shape at apex.*—Retuse.

*Margin.*—Entire.

*Aspect.*—Upward.

*Texture.*—Upper surface: Smooth. Lower surface: Smooth.

*Color of opening petals.*—Upper surface: Red group, RHS 52B. Base: White group, RHS N 155B.

*Color of opening petals.*—Lower surface: Red-purple group, RHS 58C. Base: White group, RHS N 155B.

*Color of fully opened petals.*—Upper surface: Red group, RHS 52B. Base: White group, RHS N 155B. Lower surface: Red-purple group, RHS 58C. Base color: White group RHS N 155B.

Sepals:

*Quantity per flower.*—2.

*Length.*—Abut 3 mm.

*Width.*—About 1 mm.

*Overall shape.*—Oblong.

*Apex shape.*—Rounded.

*Base shape.*—Rounded.

*Margin.*—Entire.

*Color.*—Upper surface: RHS 142B, green group. Lower surface: RHS 143A, green group.

Spur:

*Quantity per flower.*—One.

*Length.*—About 2.5 cm.

*Diameter.*—At apex: About 1 mm. At flower: About 2 mm.

*Aspect.*—Spur curvature 40°–45° from peduncle.

*Color of spur.*—Towards base: Yellow-Green, RHS 145C. Towards apex: Red-Purple, RHS 59A.

Peduncles:

*Appearance and angle.*—Erect 90° from corolla.

*Length.*—About 2 cm.

*Diameter.*—About 1 mm.

*Texture.*—Smooth.

*Strength.*—Stable, flexible.

*Color.*—Yellow-Green group, RHS N144D.

Reproductive organs: Sterile, no reproductive organs.

Disease/pest resistance: No sensitivity was observed under regular growing conditions.

Disease/pest susceptibility: No information is currently available.

Low temperature tolerance: Sensitive to temperatures below 10° C.

I claim:

1. A new and distinct Double *Impatiens* plant named 'Danmubicred', as illustrated and described herein.

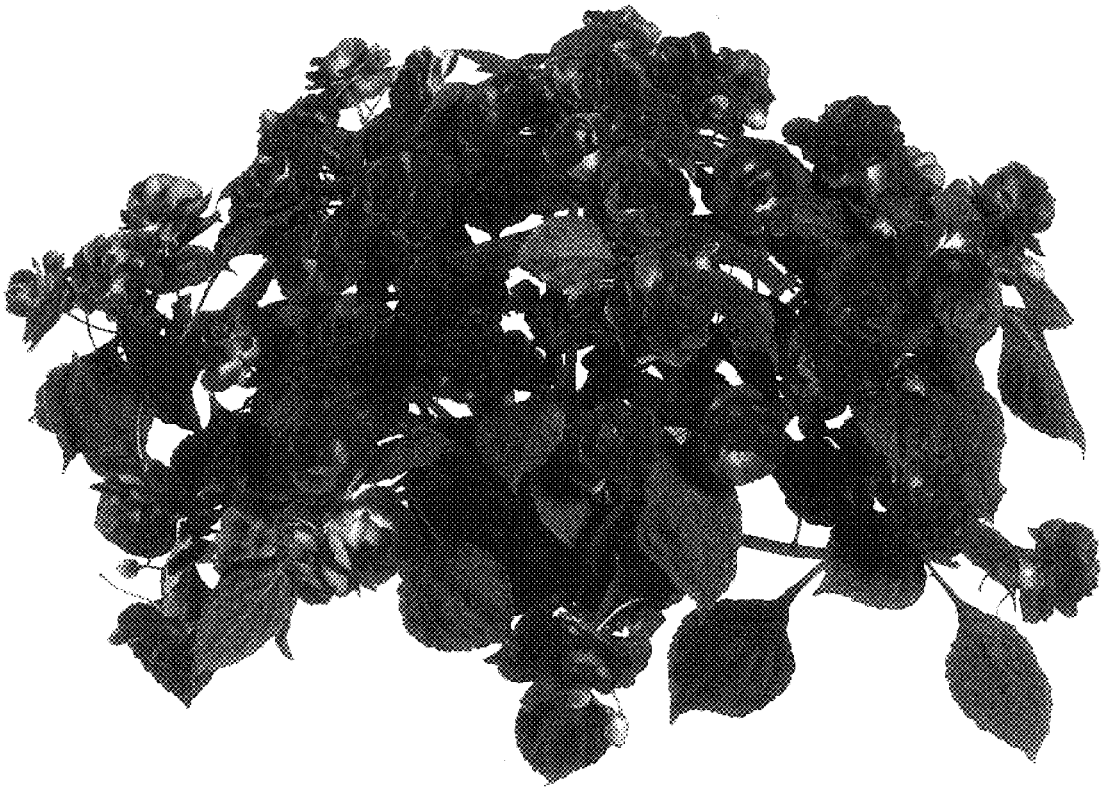

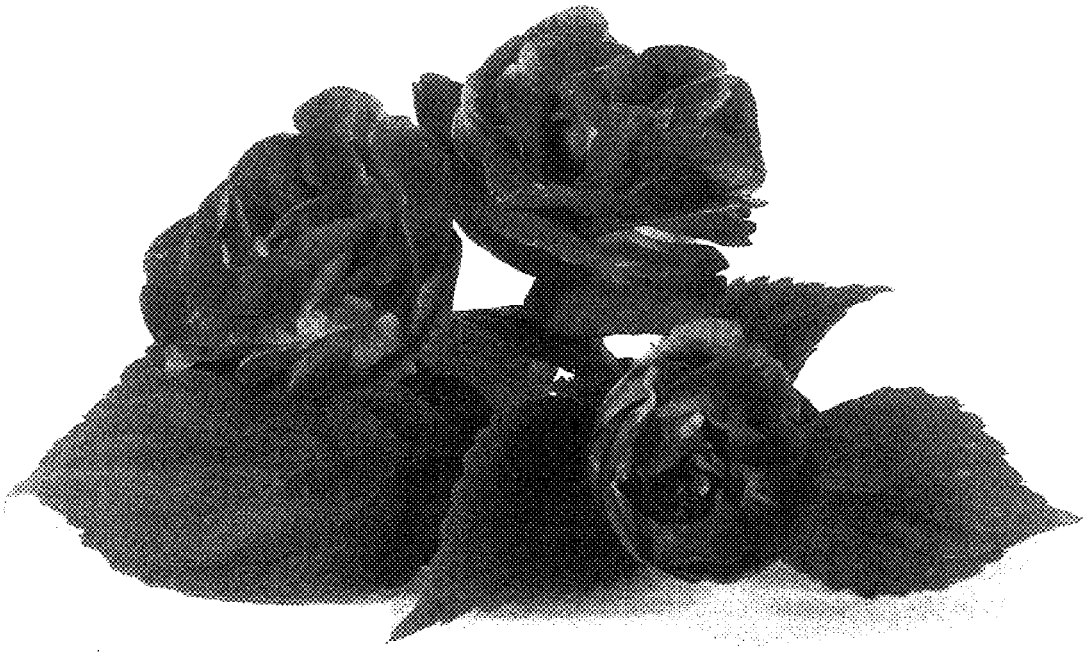

* * * * *